(12) United States Patent
Taki

(10) Patent No.: US 12,268,546 B2
(45) Date of Patent: Apr. 8, 2025

(54) INFORMATION PROCESSING APPARATUS, INFORMATION PROCESSING METHOD, AND PROGRAM

(71) Applicant: FUJIFILM CORPORATION, Tokyo (JP)

(72) Inventor: Tomoko Taki, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 296 days.

(21) Appl. No.: 17/679,105

(22) Filed: Feb. 24, 2022

(65) Prior Publication Data
US 2022/0175335 A1 Jun. 9, 2022

Related U.S. Application Data

(63) Continuation of application No. PCT/JP2020/026765, filed on Jul. 8, 2020.

(30) Foreign Application Priority Data

Sep. 27, 2019 (JP) .................................. 2019-176894
Jun. 17, 2020 (JP) .................................. 2020-104528

(51) Int. Cl.
*A61B 6/00* (2024.01)
*A61B 6/12* (2006.01)
(Continued)

(52) U.S. Cl.
CPC .............. *A61B 6/5217* (2013.01); *A61B 6/12* (2013.01); *A61B 6/505* (2013.01); *G06T 7/0012* (2013.01);
(Continued)

(58) Field of Classification Search
CPC ......... A61B 6/5217; A61B 6/12; A61B 6/505; G16H 30/40; G06T 7/0012;
(Continued)

(56) References Cited

U.S. PATENT DOCUMENTS 5,480,439 A * 1/1996 Bisek .................... A61F 2/4657
378/89
2006/0224088 A1* 10/2006 Roche .................. A61B 5/0086
600/595
(Continued)

FOREIGN PATENT DOCUMENTS

JP 2005-169041 A 6/2005
JP 2005-287813 A 10/2005
(Continued)

OTHER PUBLICATIONS

Eskandarloo, A., et al., "Association between Marginal Bone Loss and Bone Quality at Dental Implant Sites Based on Evidence from Cone Beam Computed Tomography and Periapical Radiographs," Contemporary Clinical Dentistry. vol. 10, 2019. p. 36-41 (Year: 2019).*

(Continued)

*Primary Examiner* — Sean A Frith
(74) *Attorney, Agent, or Firm* — SOLARIS Intellectual Property Group, PLLC

(57) ABSTRACT

An information processing apparatus includes a bone part image generation unit that generates a bone part image in which a bone part of a subject is highlighted, from a first radiographic image and a second radiographic image acquired by radiation having different energy distributions transmitted through the subject, a bone mineral content derivation unit that derives a bone mineral content for each pixel of the bone part image, and a postoperative information derivation unit that, based on a bone mineral content around an artificial object implanted in the bone part of the subject, derives information indicating a state of the bone part of the subject after the artificial object is implanted in the bone part of the subject, as postoperative information.

12 Claims, 14 Drawing Sheets

(51) Int. Cl.
  *A61B 6/50* (2024.01)
  *G06T 7/00* (2017.01)
  *G16H 30/40* (2018.01)
(52) U.S. Cl.
  CPC .... *G16H 30/40* (2018.01); *G06T 2207/10116* (2013.01); *G06T 2207/30008* (2013.01); *G06T 2207/30052* (2013.01)
(58) Field of Classification Search
  CPC . G06T 2207/10116; G06T 2207/30008; G06T 2207/30052
  See application file for complete search history.

(56) References Cited

U.S. PATENT DOCUMENTS

| | | | |
|---|---|---|---|
| 2016/0035089 A1* | 2/2016 | Lelong | G06T 7/0012 382/132 |
| 2016/0140720 A1* | 5/2016 | Naito | A61B 6/5211 382/132 |
| 2018/0028139 A1* | 2/2018 | Kuwabara | A61B 6/4291 |
| 2018/0146942 A1* | 5/2018 | Skalli | A61B 6/5217 |
| 2018/0263697 A1* | 9/2018 | Eskesen | G16H 30/40 |

FOREIGN PATENT DOCUMENTS

| | | | |
|---|---|---|---|
| JP | 2008-534140 A | | 8/2008 |
| JP | 2011083360 A | * | 4/2011 |
| JP | 2014-213125 A | | 11/2014 |
| JP | 2015-043959 A | | 3/2015 |
| JP | 2018-015453 A | | 2/2018 |

OTHER PUBLICATIONS

International Search Report issued in International Application No. PCT/JP2020/026765 on Sep. 8, 2020.
Written Opinion of the ISA issued in International Application No. PCT/JP2020/026765 on Sep. 8, 2020.
English language translation of the following: Office action dated Mar. 7, 2023 from the JPO in a Japanese patent application No. 2021-548360 corresponding to the instant patent application.
English language translation of the following: Office action dated Jun. 6, 2023 from the JPO in a Japanese patent application No. 2021-548360 corresponding to the instant patent application.

* cited by examiner

INFORMATION PROCESSING APPARATUS, INFORMATION PROCESSING METHOD, AND PROGRAM

CROSS REFERENCE TO RELATED APPLICATIONS

The present application is a Continuation of PCT International Application No. PCT/JP2020/026765, filed on Jul. 8, 2020, which claims priority to Japanese Patent Application No. 2019-176894, filed on Sep. 27, 2019 and Japanese Patent Application No. 2020-104528, filed on Jun. 17, 2020. Each application above is hereby expressly incorporated by reference, in its entirety, into the present application.

BACKGROUND

Technical Field

A technique of the present disclosure relates to an information processing apparatus, an information processing method, and a program.

Related Art

A Dual X-ray Absorptiometry (DXA) method is known as a representative bone mineral quantitation method used to diagnose bone density in a bone disease, such as osteoporosis. The DXA method is a method that calculates a bone mineral content from pixel values of a radiographic image obtained by imaging with radiation having two kinds of energy levels using the fact that radiation, which is incident on a human body and is transmitted through the human body, is subjected to attenuation characterized by a mass attenuation coefficient $\mu$ ($cm^2/g$) depending on a substance (for example, bone) forming the human body, density $\rho$ ($g/cm^3$) of the substance, and a thickness t (cm) of the substance.

Furthermore, a radiography apparatus that comprises two radiation detectors including a plurality of pixels, which accumulate electric charge according to irradiated radiation and the two radiation detectors are disposed to be stacked is known. In addition, a technique that measures a bone mineral content of a subject using each electric signal according to a dose of radiation irradiated to each radiation detector in this kind of radiography apparatus is known (see JP2018-15453A).

There is known a method that searches for an optimum artificial medical material in a replacement operation with an artificial medical material (see JP2005-287813A). The method includes the following steps: (a) a step of obtaining a tomographic image of a disease part of a patient who needs a replacement operation of an artificial medical material, (b) a step of creating three-dimensional shape data by recomposing obtained tomographic image data in a three-dimensional shape, (c) a step of adapting the three-dimensional shape data obtained in the step (b) to three-dimensional shape data of artificial medical materials in a database including the three-dimensional shape data of the artificial medical materials constructed in advance, and (d) a step of selecting an artificial medical material having a shape adapting to a tissue of the disease part of the patient with which the artificial medical material is to be joined.

An artificial object, such as an artificial bone, is implanted in a living body by a surgical operation to replace a bone lost due to comminuted fracture, tumor, or the like. Furthermore, an artificial object is used for filling a bone defect part generated in a spinal operation or an artificial joint operation.

A state of recovery of a bone part of a patient after an operation to implant an artificial object in the bone part is performed is recognized by a physician visually confirming an image for diagnosis, such as an X-ray image, a Computed Tomography (CT) image, or a Magnetic Resonance Imaging (MRI) image, obtained by imaging the bone part. However, according to a diagnosis method through such visual confirmation of the image for diagnosis by the physician, variation may occur in a diagnosis result depending on the experience of the like of the physician.

SUMMARY OF THE INVENTION

The technique of the present disclosure has been accomplished in view of the above-described points, and an object of the technique of the present disclosure is to enable accurate recognition on a state of a bone part of a patient after an operation to implant an artificial object in the bone part is performed.

An information processing apparatus according to the technique of the present disclosure comprises a bone part image generation unit that generates a bone part image in which a bone part of a subject is highlighted, from a first radiographic image and a second radiographic image acquired by radiation having different energy distributions transmitted through the subject, a bone mineral content derivation unit that derives a bone mineral content for each pixel of the bone part image, and a postoperative information derivation unit that, based on a bone mineral content around an artificial object implanted in the bone part of the subject, derives information indicating a state of the bone part of the subject after the artificial object is implanted in the bone part of the subject, as postoperative information.

The postoperative information derivation unit may derive a numerical value depending on a difference between a bone mineral content at a position relatively close to the artificial object and a bone mineral content at a position relatively far from the artificial object, as the postoperative information.

The postoperative information derivation unit may derive information indicating time transition of the numerical value depending on the difference between the bone mineral content at the position relatively close to the artificial object and the bone mineral content at the position relatively far from the artificial object, as the postoperative information.

The postoperative information derivation unit may derive information indicating a relationship between a distance from the artificial object and a bone mineral content, as the postoperative information.

The postoperative information derivation unit may derive a numerical value depending on a difference between a bone mineral content around a planned implant region of the artificial object before the artificial object is implanted in the bone part of the subject and the bone mineral content around the artificial object after the artificial object is implanted in the bone part of the subject, as the postoperative information.

The postoperative information derivation unit may specify a region of a cancellous bone forming the bone part based on the bone mineral content of each pixel of the bone part image and may derive information indicating a state of the cancellous bone of the subject based on a bone mineral content of the cancellous bone around an artificial object implanted in the cancellous bone of the subject, as the postoperative information.

The postoperative information derivation unit may specify regions of a cancellous bone and a cortical bone forming the bone part based on the bone mineral content of each pixel of the bone part image and may derive information indicating the state of the bone part of the subject based on a bone mineral content of at least one of the cancellous bone or the cortical bone around the artificial object implanted in the bone part of the subject, as the postoperative information.

The information processing apparatus may further comprise a bone strength derivation unit that derives bone strength for each pixel of the bone part image based on the bone mineral content of each pixel of the bone part image.

The information processing apparatus may further comprise an operation plan information derivation unit that derives an area of a region having a bone mineral content greater than a predetermined threshold value or bone strength higher than a predetermined threshold value in a planned region where the artificial object is implanted, based on the bone mineral content or bone strength of each pixel of the bone part image and determines whether or not an operation to implant the artificial object in the bone part of the subject is possible, based on the area.

The operation plan information derivation unit may derive a recommended region where the artificial object is to be implanted, based on the bone mineral content or bone strength of each pixel of the bone part image.

The bone part image generation unit may eliminate a scattered ray component from the first radiographic image and the second radiographic image based on a radiation characteristic of an object interposed between the subject and a radiation detector for acquiring the first radiographic image or the second radiographic image.

An information processing method according to the technique of the present disclosure comprises generating a bone part image in which a bone part of a subject is highlighted, from a first radiographic image and a second radiographic image acquired by radiation having different energy distributions transmitted through the subject, deriving a bone mineral content for each pixel of the bone part image, and, based on a bone mineral content around an artificial object implanted in the bone part of the subject, deriving information indicating a state of the bone part of the subject after the artificial object is implanted in the bone part of the subject, as postoperative information.

A program according to the technique of the present disclosure causes a computer to execute a process comprising generating a bone part image in which a bone part of a subject is highlighted, from a first radiographic image and a second radiographic image acquired by radiation having different energy distributions transmitted through the subject, deriving a bone mineral content for each pixel of the bone part image, and, based on a bone mineral content around an artificial object implanted in the bone part of the subject, deriving information indicating a state of the bone part of the subject after the artificial object is implanted in the bone part of the subject, as postoperative information.

According to the technique of the present disclosure, it is possible to enable accurate recognition of a state of a bone part of a patient after an operation to implant an artificial object in the bone part is performed.

DETAILED DESCRIPTION

Figure 1:
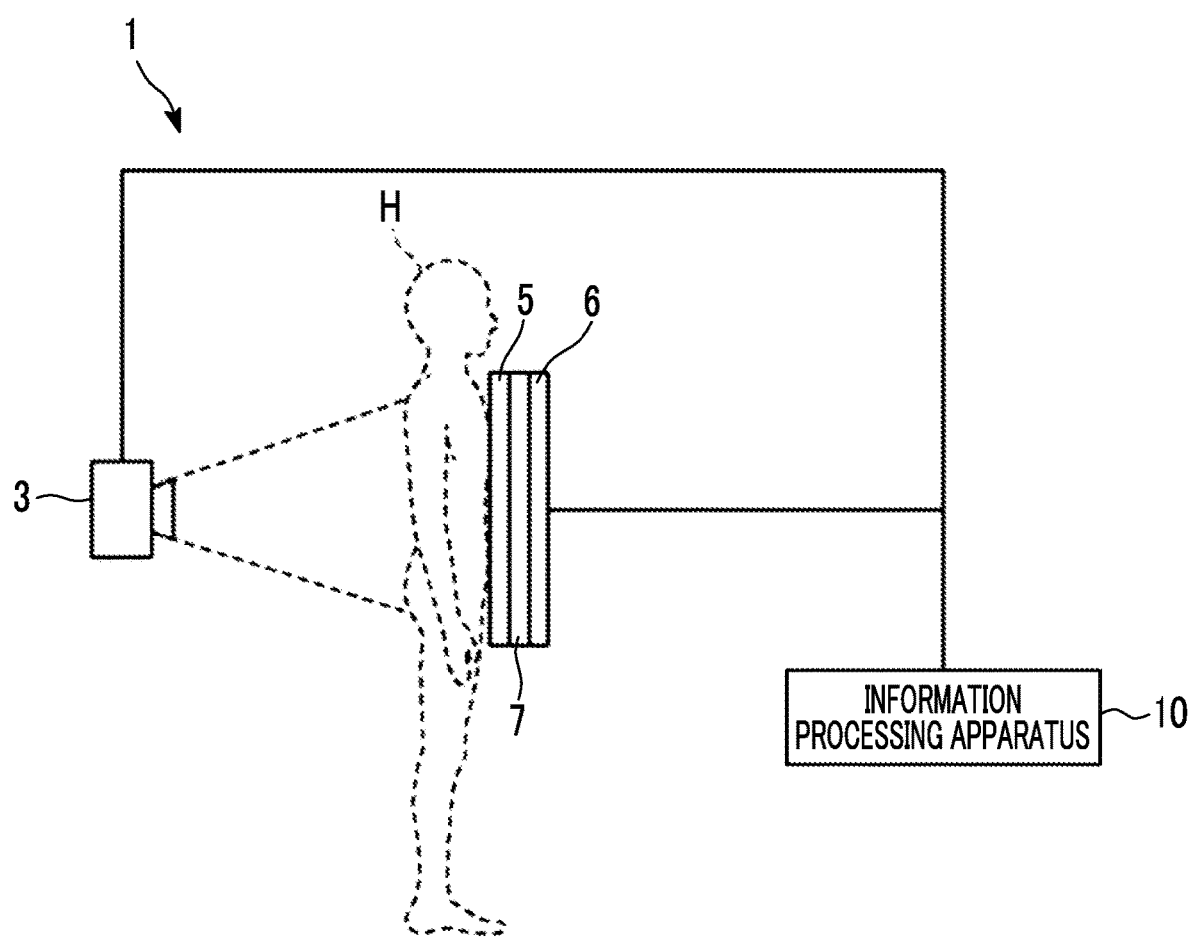
FIG. 1 is a schematic block diagram showing the configuration of a radiography system according to an embodiment of the technique of the present disclosure.

Hereinafter, an embodiment of the technique of the present disclosure will be described referring to the drawings. In the respective drawings, the substantially same or equivalent components are represented by the same reference numerals.

FIG. 1 is a schematic block diagram showing the configuration of a radiography system 1 according to the embodiment of the technique of the present disclosure. The radiography system 1 includes an X-ray source 3, a first radiation detector 5, a second radiation detector 6, an X-ray energy conversion filter 7, and an information processing apparatus 10.

Each of the first and second radiation detectors 5 and 6 generates a radiographic image based on X-rays emitted from the X-ray source 3 and transmitted through a subject H. The first and second radiation detectors 5 and 6 may have a form of a so-called flat panel detector (FPD) in which a radiographic image signal is read out by turning on and off a thin film transistor (TFT) switch. In this case, the first and second radiation detectors 5 and 6 may be a direct radiation detector that is directly irradiated with radiation to generate electric charge or may be an indirect radiation detector that converts radiation into visible light once and converts the visible light into an electric charge signal. The first and second radiation detectors 5 and 6 may be a radiation detector to which a Computed Radiography (CR) technique for reading an image recorded on an imaging plate through irradiation of a laser beam is applied. The X-ray energy conversion filter 7 is configured of a metal plate, such as a copper plate, capable of absorbing a specific energy component included in X-rays.

A radiographic image is captured in a state in which the first radiation detector 5, the X-ray energy conversion filter 7, and the second radiation detector 6 are superimposed in this order, whereby one-shot energy subtraction is realized. That is, two radiographic images having different energy distributions are acquired from the first radiation detector 5 and the second radiation detector 6.

In the first radiation detector 5, a first radiographic image G1 of the subject H by low-energy X-rays including so-called soft rays is acquired. In the second radiation detector 6, a second radiographic image G2 of the subject H by high-energy X-rays excluding soft rays is acquired. The first and second radiographic images are input to the information processing apparatus 10.

In the embodiment, in imaging the subject H, a scattered ray elimination grid that eliminates scattered ray components of X-rays transmitted through the subject H is not used. For this reason, primary ray components and scattered ray components of X-rays transmitted through the subject H are included in the first radiographic image G1 and the second radiographic image G2.

Based on the first radiographic image G1 and the second radiographic image G2 acquired on the subject H who has an operation to implant an artificial object, such as an artificial bone, in a bone part, the information processing apparatus 10 has a function of deriving postoperative information indicating a state of the bone part after the operation.

Figure 2:
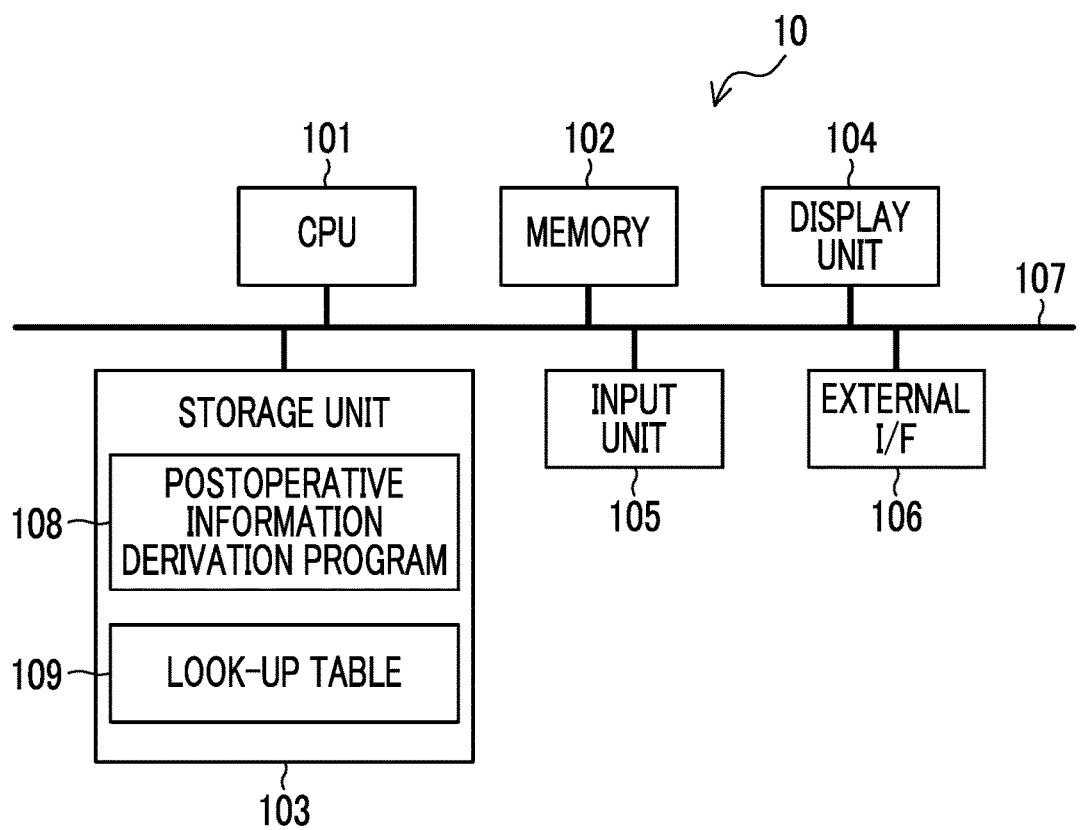
FIG. 2 is a diagram showing an example of the hardware configuration of an information processing apparatus according to the embodiment of the technique of the present disclosure.

FIG. 2 is a diagram showing an example of the hardware configuration of the information processing apparatus 10. The information processing apparatus 10 includes a central processing unit (CPU) 101, a memory 102, a storage unit 103, a display unit 104, such as a liquid crystal display, an input unit 105, such as a keyboard and a mouse, and an external interface (I/F) 106. The CPU 101, the memory 102, the storage unit 103, the display unit 104, the input unit 105, and the external I/F 106 are connected to a bus 107. The first and second radiation detectors 5 and 6 are connected to the external I/F 106. The information processing apparatus 10 may configure, for example, a personal computer or a server computer.

The storage unit 103 is realized by a hard disk drive (HDD), a solid state drive (SSD), a flash memory, or the like. A postoperative information derivation program 108 is stored in the storage unit 103 as a storage medium. The CPU 101 reads out the postoperative information derivation program 108 from the storage unit 103, develops the postoperative information derivation program 108 to the memory 102, and executes the developed postoperative information derivation program 108. Furthermore, a look-up table 109 described below is stored in the storage unit 103.

The display unit 104 is composed of a display, such as a cathode ray tube (CRT) or a liquid crystal display, and displays a radiographic image and the like acquired by imaging or assists various inputs needed for processing that is executed in the information processing apparatus 10.

The input unit 105 is composed of an input device, such as a keyboard, a mouse, or a touch panel type, and receives an operator's instruction for an operation of the information processing apparatus 10.

Figure 3:
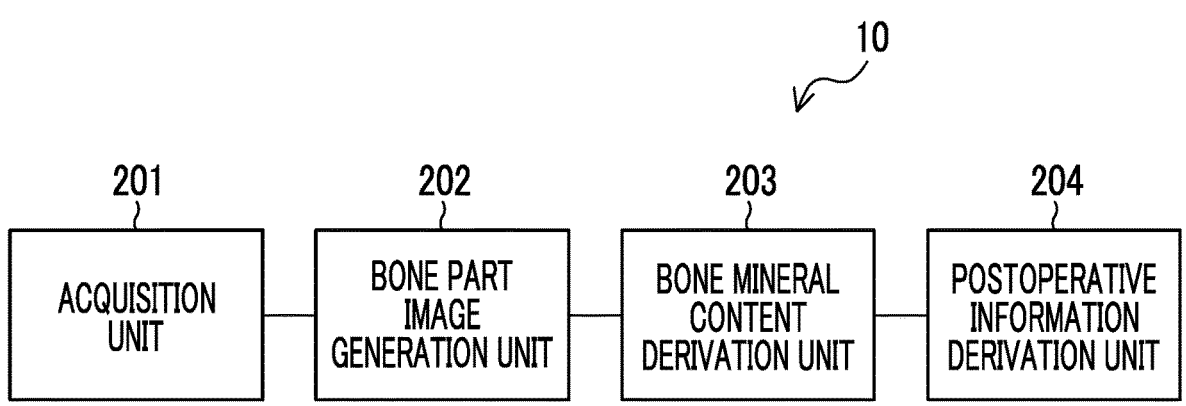
FIG. 3 is a functional block diagram showing an example of the functional configuration of the information processing apparatus according to the embodiment of the technique of the present disclosure.

FIG. 3 is a functional block diagram showing an example of the functional configuration of the information processing apparatus 10. The information processing apparatus 10 includes an acquisition unit 201, a bone part image generation unit 202, a bone mineral content derivation unit 203, and a postoperative information derivation unit 204. The information processing apparatus 10 functions as the acquisition unit 201, the bone part image generation unit 202, the bone mineral content derivation unit 203, and the postoperative information derivation unit 204 by the CPU 101 executing the postoperative information derivation program 108.

The acquisition unit 201 acquires the first radiographic image G1 and the second radiographic image G2 acquired by X-ray having different energy distributions transmitted through the subject H. In imaging the first radiographic image G1 and the second radiographic image G2, imaging conditions, such as an irradiation dose of X-ray, a tube voltage, and a source-to-image receptor distance (SID) (a distance between an X-ray tube focus and an image receiving surface), are set. The set imaging conditions are stored in the storage unit 103.

The bone part image generation unit 202 generates a bone part image Gb in which the bone part of the subject H is highlighted, from the first radiographic image G1 and the second radiographic image G2. Specifically, the bone part image generation unit 202 performs weighting subtraction between corresponding pixels for the first radiographic image G1 and the second radiographic image G2, for example, as shown in Expression (1) described below, thereby generating the bone part image Gb. In Expression (1), $\mu$ is a weighting factor, and x and y are coordinates of each pixel of the bone part image Gb.

$$Gb(x,y)=G1(x,y)-\mu \times G2(x,y) \qquad (1)$$

Scattered ray components may be eliminated from the first radiographic image G1 and the second radiographic image G2, and in addition, a soft part image and the bone part image, for example, using a method described in JP2015-043959A. The first radiographic image G1 and the second radiographic image G2 are different in content of scattered rays because of a difference in distance from the subject H. For this reason, the difference in content of scattered rays between the first radiographic image G1 and the second radiographic image G2 may be corrected.

The bone mineral content derivation unit 203 derives a bone mineral content B for each pixel of the bone part image Gb. In the embodiment, the bone mineral content derivation unit 203 derives the bone mineral content B by converting each pixel value of the bone part image Gb into a pixel value of a bone image in a case of being acquired under a reference imaging condition. More specifically, the bone mineral content derivation unit 203 derives the bone mineral content B by correcting each pixel value of the bone part image Gb using a correction coefficient acquired from the look-up table 109 described below.

Here, as the tube voltage in the X-ray source 3 is higher and X-rays emitted from the X-ray source 3 have high energy, contrast of a soft part and a bone part in a radiographic image is smaller. Furthermore, in a process in which X-rays are transmitted through the subject H, a low-energy component of X-rays is absorbed by the subject H, and beam hardening that X-rays increase in energy occurs. The increase in energy of X-rays due to beam hardening is greater as the body thickness of the subject H is greater.

Figure 4:
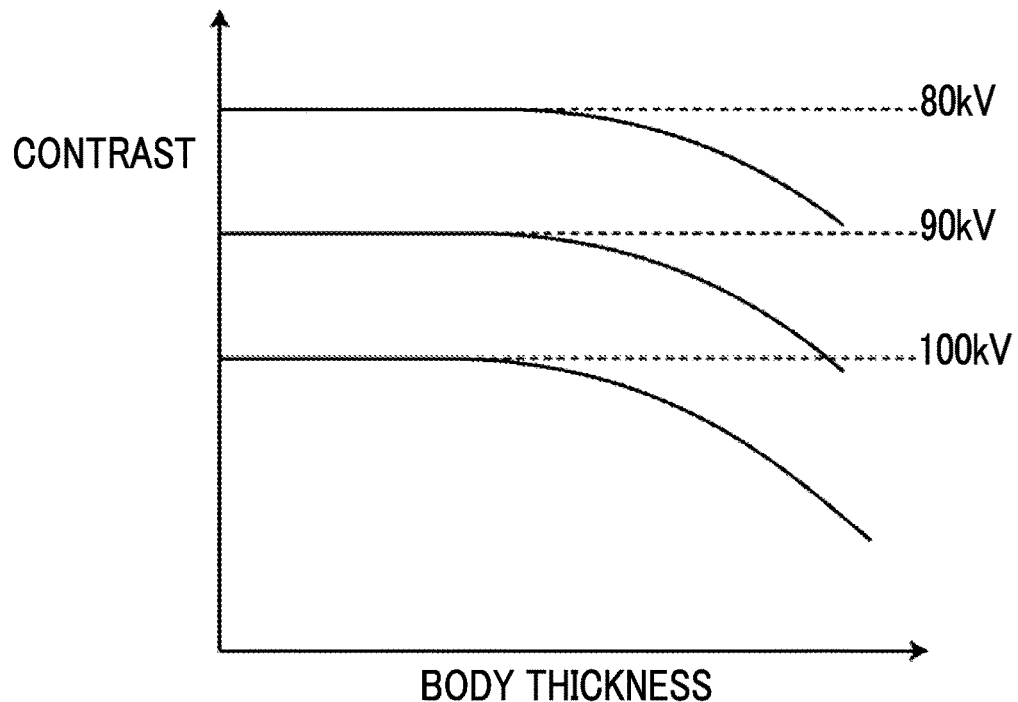
FIG. 4 is a diagram showing a relationship between a body thickness of a subject and contrast of a bone part and a soft part.

FIG. 4 is a diagram showing a relationship between the body thickness of the subject H and contrast of a bone part and a soft part. FIG. 4 shows a relationship between the body thickness of the subject H and the contrast of the bone part and the soft part at three tube voltages of 80 kV, 90 kV, and 100 kV. As shown in FIG. 4, the contrast is lower as the tube voltage is higher. In a case where the body thickness of the subject H exceeds a certain value, the contrast is lower as the body thickness is greater. As a pixel value of a bone part region in the bone part image Gb is greater, the contrast of the bone part and the soft part is higher. For this reason, the relationship shown in FIG. 4 shows that shift to a higher contrast side is made as the pixel value of the bone part region in the bone part image Gb is greater.

In the embodiment, the look-up table 109 for acquiring the correction coefficient for correcting a difference in contrast depending on the tube voltage at the time of imaging and a decrease in contrast under the influence of beam hardening in the bone part image Gb is stored in the storage unit 103. The correction coefficient is a coefficient for correcting each pixel value of the bone part image Gb.

Figure 5:
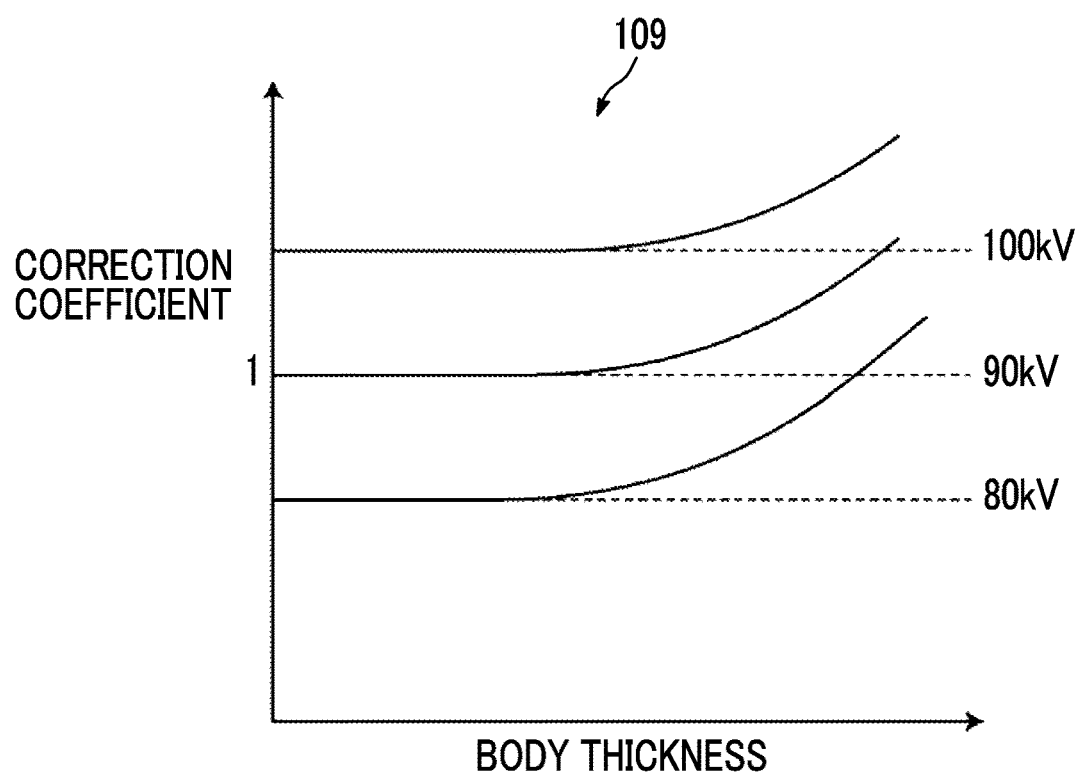
FIG. 5 is a diagram showing an example of a look-up table according to the embodiment of the technique of the present disclosure.

FIG. 5 is a diagram showing an example of the look-up table 109. In FIG. 5, a look-up table in which a reference imaging condition of a tube voltage 90 kV is set is illustrated. As shown in FIG. 5, in the look-up table 109, as the tube voltage is greater and as the body thickness of the subject is greater, a greater correction coefficient is set. In the example shown in FIG. 5, since the reference imaging condition is the tube voltage 90 kV, in a case where the tube voltage is 90 kV and the body thickness is 0, the correction coefficient is 1. In FIG. 5, although the look-up table 109 is shown in a two-dimensional manner, the correction coefficient is different depending on the pixel value of the bone part region. For this reason, the look-up table 109 is actually a three-dimensional table in which an axis representing the pixel value of the bone part region is added.

The bone mineral content derivation unit 203 derives a body thickness distribution T(x,y) of the subject H to extract a correction coefficient depending on the body thickness of the subject H from the look-up table 109. In the embodiment, the bone mineral content derivation unit 203 uses the first radiographic image G1 acquired by the radiation detector 5 close to the subject H in estimating the body thickness of the subject H. Note that the second radiographic image G2 may be used. Weighting subtraction may be performed between corresponding pixels for the first radiographic image G1 and the second radiographic image G2 to generate a soft part image in which a soft part of the subject H included in each radiographic image is highlighted, and the body thickness of the subject H may be estimated using the soft part image. Even in a case where any image is used, a low frequency image representing a low frequency component of the image may be generated and the body thickness may be estimated using the low frequency image.

The bone mineral content derivation unit 203 may derive the body thickness distribution T(x,y) of the subject H, for example, using the method described in JP2015-043959A. In the following description, an example of a method of deriving the body thickness distribution T(x,y) of the subject H will be described.

First, the bone mineral content derivation unit 203 acquires a virtual model K of the subject H having an initial body thickness distribution $T0(x,y)$. The virtual model K is data that virtually represents the subject H and has the body thickness involving the initial body thickness distribution $T0(x,y)$ corresponding to a coordinate position of each pixel of the first radiographic image G1. The virtual model K of the subject H having the initial body thickness distribution $T0(x,y)$ may be stored in advance in the storage unit 103.

Next, the bone mineral content derivation unit 203 acquires an estimated primary ray image of a primary ray image to be obtained by imaging the virtual model K and an estimated scattered ray image of a scattered ray image to be obtained by imaging the virtual model K based on the initial body thickness distribution $T0(x,y)$ of the virtual model K and imaging conditions in a case where the first radiographic image G1 is acquired. Then, an image in which the estimated primary ray image and the estimated scattered ray image are composed is generated as an estimated image of the first radiographic image G1 to be obtained by imaging the subject H.

Next, the bone mineral content derivation unit 203 corrects the initial body thickness distribution $T0(x,y)$ of the virtual model K such that a difference between the estimated image and the first radiographic image G1 decreases. The bone mineral content derivation unit 203 repeatedly generates the estimated image and corrects the body thickness distribution until the difference between the estimated image and the first radiographic image G1 satisfies a predetermined end condition. The bone mineral content derivation unit 203 derives the body thickness distribution in a case where the end condition is satisfied, as the body thickness distribution T(x,y) of the subject H. In the bone part image generation unit 202, the scattered ray component can be eliminated from the first radiographic image G1 by subtracting the estimated scattered ray image in a case where the body thickness distribution satisfying the end condition is acquired, from the first radiographic image G1. The scattered ray component can also be eliminated from the second radiographic image G2 in a similar manner.

The bone mineral content derivation unit 203 extracts a correction coefficient $C0(x,y)$ of each pixel depending on the derived body thickness distribution T(x,y) of the subject H and the imaging conditions including a set value of the tube voltage stored in the storage unit 103, from the look-up table 109. Then, as shown in Expression (2) described below, the bone mineral content derivation unit 203 derives a bone mineral content B(x,y) of each pixel of the bone part image Gb by multiplying each pixel (x,y) of the bone part region in the bone part image Gb by the correction coefficient $C0(x,y)$. The bone mineral content B(x,y) derived in this manner represents a pixel value of a bone part of a bone part region included in a radiographic image that is acquired by imaging the subject H at the tube voltage of 90 kV as the reference imaging condition, and from which the influence of beam hardening is eliminated.

$$B(x,y)=C0(x,y) \times Gb(x,y) \qquad (2)$$

Based on a bone mineral content around an artificial object, such as an artificial bone, implanted in a bone part of the subject, the postoperative information derivation unit 204 derives information indicating a state of the bone part of the subject after the artificial object is implanted in the bone part of the subject, as postoperative information. An artificial object, such as an artificial bone, is implanted in a living body by a surgical operation to replace a bone lost due to comminuted fracture, tumor, or the like.

Figure 6:
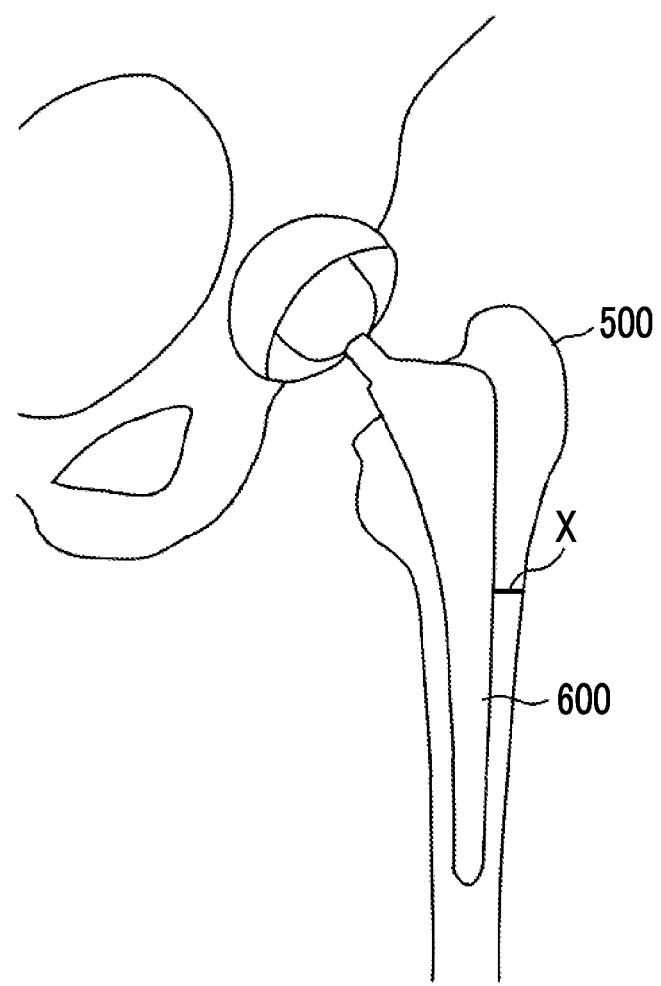
FIG. 6 is a diagram showing an example of an artificial bone implanted in a bone part of a subject.

FIG. 6 is a diagram showing an example of an artificial bone implanted in a bone part of a subject. FIG. 6 illustrates the bone part of the subject who has an artificial joint replacement operation, and a stem 600 of an artificial joint is implanted in a thighbone 500 of the subject.

As a method of fixing the stem 600, a direct fixing method (cementless fixing) and an indirect fixing method (cemented fixing) are known. In the direct fixing method, the stem 600 is inserted into a cavity inside the thighbone 500 without using cement. A shape of the cavity inside the thighbone 500 is adjusted in advance such that the stem 600 fits in the cavity. A surface of the stem 600 is roughened, and a bone tissue is growing to infiltrate inward of the stem 600. That is, immediately after the stem 600 is implanted in the thighbone 500, there is a cavity between the stem 600 and the thighbone 500; however, in a case where the thighbone 500 is recovered, the cavity is reduced and disappears along with the growth of the bone tissue. Accordingly, it is possible to recognize a degree of recovery of the thighbone 500 after the operation by acquiring a bone mineral content B around the stem 600.

Figure 7:
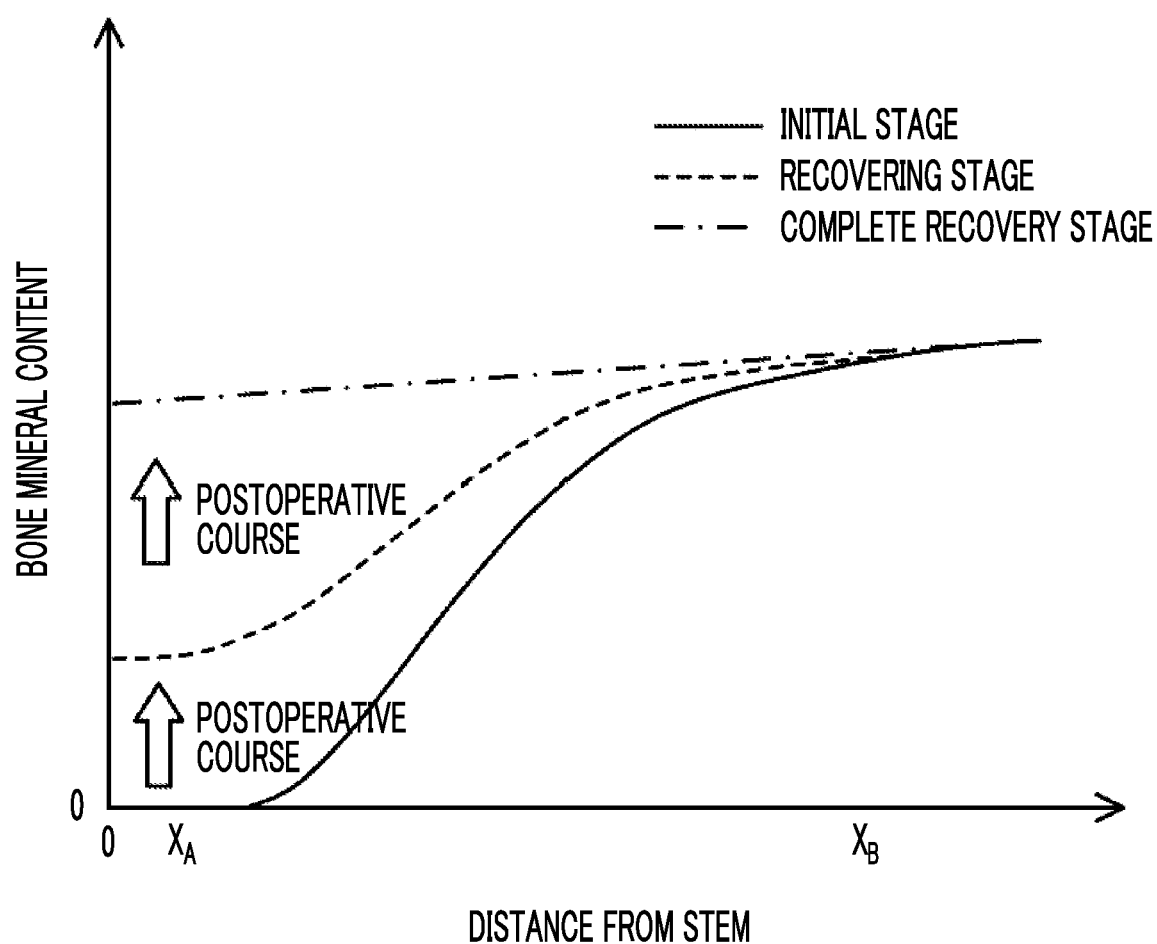
FIG. 7 is a graph showing an example of a relationship between a distance from a stem inside a thighbone and a bone mineral content in each stage after an operation.

FIG. 7 is a graph showing an example of a relationship between a distance from the stem 600 inside the thighbone 500 and the bone mineral content B in each stage after an operation. The horizontal axis of the graph shown in FIG. 7 is a position along a line X in FIG. 6. In FIG. 7, a solid line corresponds to an initial stage immediately after the stem 600 is implanted in the thighbone 500, a dotted line corresponds to a recovering stage, and a one-dot chain line corresponds to a complete recovery stage. As shown in FIG. 7, in the initial stage after the operation, the thighbone 500 and the stem 600 are not closely attached, and a bone mineral content B near the stem 600 is extremely low. Along with recovering, the bone tissue is growing to infiltrate inward the stem 600, whereby the bone mineral content B near the stem 600 increases. On the other hand, the bone mineral content B at a position far from the stem 600 is substantially constant in each stage after the operation. In the complete recovery stage, the bone mineral content B near the stem 600 and the bone mineral content B at the position far from the stem 600 are made substantially equal.

Hereinafter, in regard to an aspect where the postoperative information derivation unit 204 derives the postoperative information, a case where the subject has the artificial joint replacement operation shown in FIG. 6 will be described as an example. The postoperative information derivation unit 204 derives a numerical value K depending on a difference between a bone mineral content $B_A$ at a position $X_A$ relatively close to the stem 600 and a bone mineral content $B_B$ at a position $X_B$ relatively far from the stem 600, as the postoperative information. For example, the postoperative information derivation unit 204 may derive a difference ($K=B_B-B_A$) in bone mineral content as the postoperative information. In this case, the numerical value derived as the postoperative information decreases along with recovery and approaches 0. The postoperative information derivation unit 204 may derive a ratio ($K=B_A/B_B$) of the bone mineral contents as the postoperative information. In this case, a numerical value derived as the postoperative information increases along with the recovery of the bone part and approaches 1. That is, it can be said that the numerical value K depending on the difference between the bone mineral contents $B_A$ and $B_B$ is a numerical value indicating the degree of recovery of the bone part after the operation. Accordingly, it is possible to quantitatively recognize the degree of recovery of the thighbone 500 after the operation by deriving the numerical value K as the postoperative information. The postoperative information derivation unit 204 displays the derived postoperative information on the display unit 104.

The postoperative information derivation unit 204 derives postoperative information using the bone mineral content B of each pixel of the bone part image Gb derived by the bone mineral content derivation unit 203. Even in any image of the first radiographic image G1, the second radiographic image G2, or the bone part image Gb, since a pixel value of the stem 600 is remarkably different from a pixel value in a bone part region, it is possible to specify a region where the stem 600 is present on each image described above. Accordingly, the postoperative information derivation unit 204 can specify the distance from the stem 600 based on any one image of the first radiographic image G1, the second radiographic image G2, or the bone part image Gb.

Figure 8:
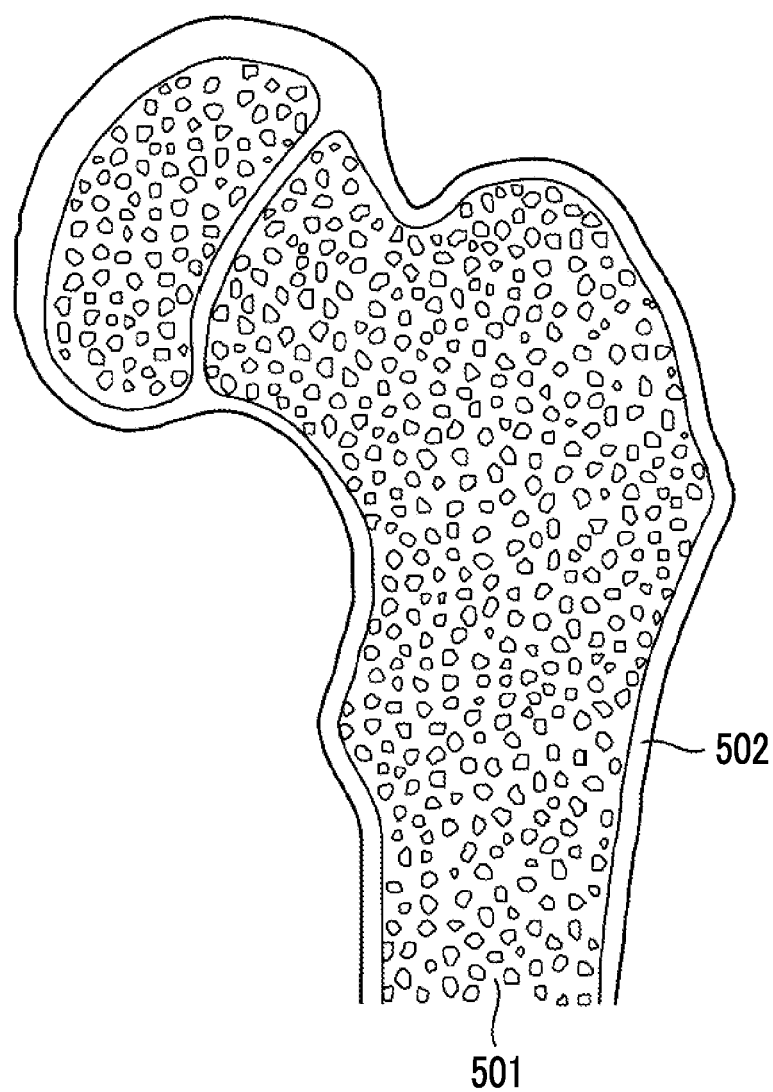
FIG. 8 is a sectional view showing an example of a cross-sectional structure of a bone of a human.

FIG. 8 is a sectional view showing an example of a cross-sectional structure of a bone of a human. As shown in FIG. 8, the bone of the human includes a cancellous bone 501, and a cortical bone 502 that covers the outside of the cancellous bone 501. The cortical bone 502 is harder and denser than the cancellous bone 501. The cancellous bone 501 is an aggregate of trabecula of small bones, called bone trabecula spreading into a bone marrow cavity. Forms of bone trabecula include a plate-shaped structure and a rod-shaped structure, and such structures are connected. Since a bone mineral content of the cancellous bone 501 is remarkably different from a bone mineral content of the cortical bone 502, it is possible to distinguish between the cortical bone 502 and the cancellous bone 501 from the bone mineral content B of each pixel of the bone part image Gb.

In a case where the artificial object is implanted in the cancellous bone 501, the postoperative information derivation unit 204 may specify a region of the cancellous bone 501 based on the bone mineral content B of each pixel of the bone part image Gb and may derive postoperative information based on the bone mineral content of the cancellous bone 501 around the artificial object. Specifically, the postoperative information derivation unit 204 may derive a numerical value K depending on a difference between a bone mineral content $B_A$ at a position $X_A$ in the cancellous bone 501 relatively close to the artificial object and a bone mineral content $B_B$ at a position $X_B$ in the cancellous bone 501 relatively far from the artificial object, as postoperative information.

On the other hand, in a case where the artificial object is implanted in the cortical bone 502, it is preferable that the postoperative information derivation unit 204 specifies a region of the cortical bone 502 based on the bone mineral content B of each pixel of the bone part image Gb and derives postoperative information based on a bone mineral content of the cortical bone 502 around the artificial object. Specifically, the postoperative information derivation unit 204 may derive a numerical value K depending on a difference between a bone mineral content $B_A$ at a position $X_A$ in the cortical bone 502 relatively close to the artificial object and a bone mineral content $B_B$ at a position $X_B$ in the cortical bone 502 relatively far from the artificial object, postoperative information.

In a case where the artificial object implanted in the bone part of the subject extends to both the cancellous bone 501 and the cortical bone 502, the regions of the cancellous bone 501 and the cortical bone 502 may be specified based on the bone mineral content B of each pixel of the bone part image Gb, and postoperative information may be derived based on the bone mineral contents of both the cancellous bone 501 and the cortical bone 502 around the artificial object. Specifically, the postoperative information derivation unit 204 may derive a numerical value K1 depending on a difference between a bone mineral content $B_{A1}$ at a position $X_{A1}$ in the cancellous bone 501 relatively close to the artificial object and a bone mineral content $B_{B1}$ at a position $X_{B1}$ in the cancellous bone 501 relatively far from the artificial object, as postoperative information, and may derive a numerical value K2 depending on a difference between a bone mineral content $B_{A2}$ at a position $X_{A2}$ in the cortical bone 502 relatively close to the artificial object and a bone mineral content $B_{B2}$ at a position $X_{B2}$ in the cortical bone 502 relatively far from the artificial object, as postoperative information. In a case where the artificial object implanted in the bone part of the subject extends to both the cancellous bone 501 and the cortical bone 502, postoperative information may be derived based on the bone mineral content of any one of the cancellous bone 501 or the cortical bone 502 around the artificial object. That is, one of the numerical value K1 or the numerical value K2 may be derived as postoperative information.

Figure 9:
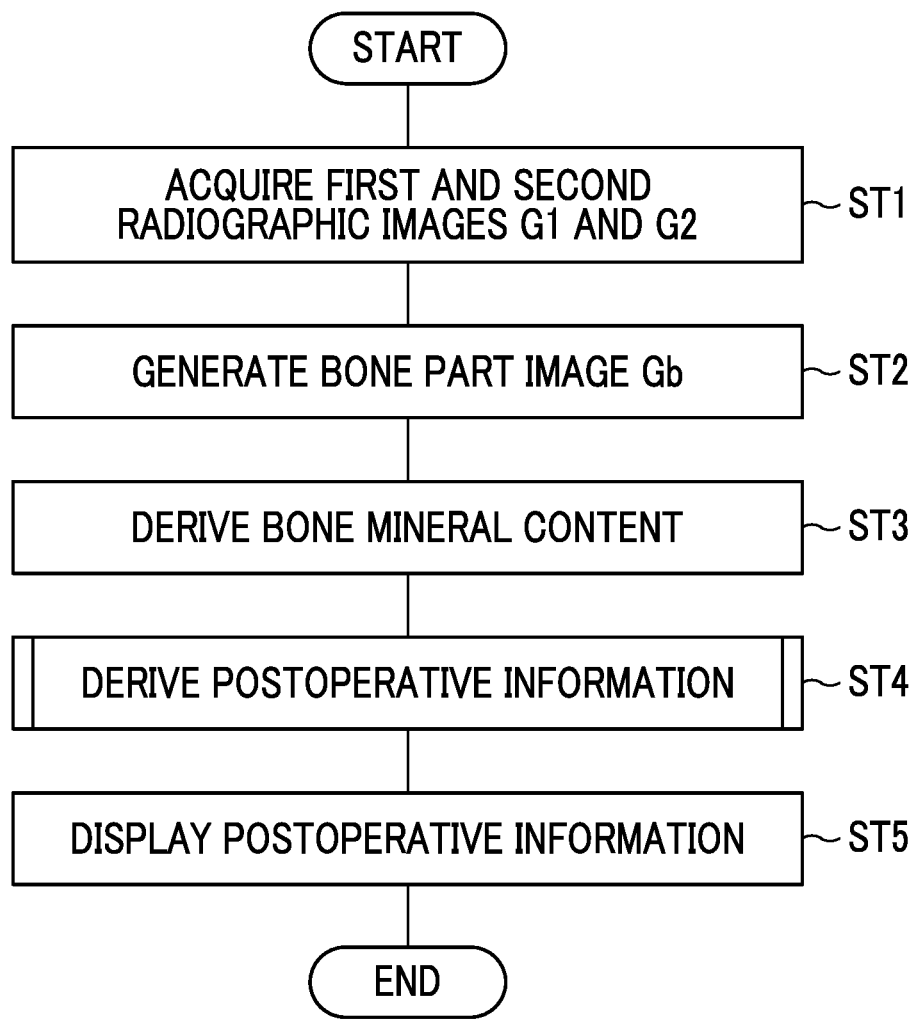
FIG. 9 is a flowchart illustrating an example of a flow of postoperative information derivation processing according to the embodiment of the technique of the present disclosure.

Hereinafter, the operations of the information processing apparatus 10 will be described. FIG. 9 is a flowchart illustrating an example of a flow of postoperative information derivation processing that is executed by the CPU 101 executing the postoperative information derivation program 108. The postoperative information derivation program 108 is executed, for example, in a case where an instruction to start execution is input by a user through the input unit 105.

In Step ST1, the acquisition unit 201 acquires the first radiographic image G1 and the second radiographic image G2 captured for a patient as the subject who has an operation to implant the artificial object in the bone part, from the first radiation detector 5 and the second radiation detector 6, respectively.

In Step ST2, the bone part image generation unit 202 performs weighting subtraction shown in Expression (1) between corresponding pixels in the first radiographic image G1 and the second radiographic image G2, thereby generating the bone part image Gb in which the bone part of the subject is highlighted.

In Step ST3, the bone mineral content derivation unit 203 derives the bone mineral content B for each pixel of the bone part image Gb by correcting each pixel value of the bone part image Gb using the correction coefficient acquired from the look-up table 109.

In Step ST4, based on the bone mineral content B around the artificial object implanted in the bone part of the subject, the postoperative information derivation unit 204 derives information indicating the state of the bone part of the subject after the artificial object is implanted in the bone part of the subject, as the postoperative information.

Figure 10:
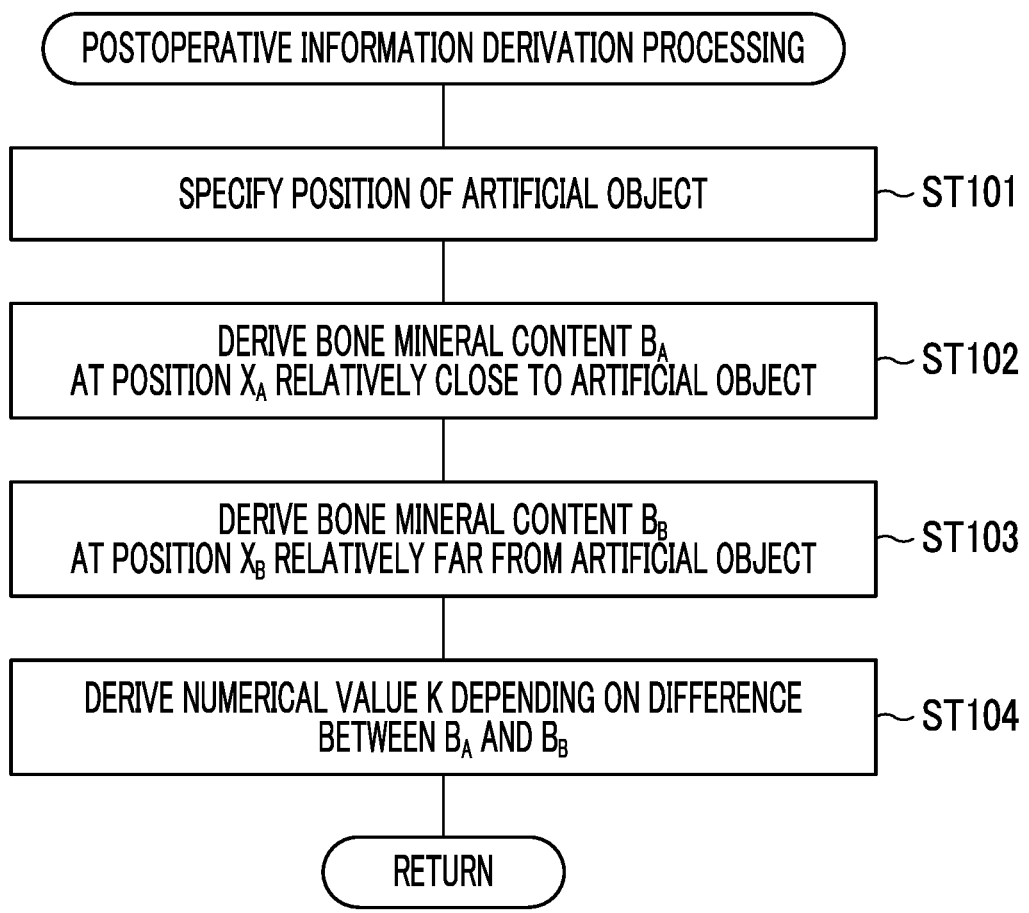
FIG. 10 is a flowchart illustrating an example of processing of deriving postoperative information according to the embodiment of the technique of the present disclosure.

FIG. 10 is a flowchart illustrating an example of the processing that is executed in Step ST4. In Step ST101, the postoperative information derivation unit 204 specifies the position of the artificial object implanted in the bone part of the subject based on any one image of the first radiographic image G1, the second radiographic image G2, or the bone part image Gb. Even in any image of the first radiographic image G1, the second radiographic image G2, or the bone part image Gb, since the pixel value of the artificial object is remarkably different from the pixel value in the bone part region, it is possible to specify the position of the artificial object in each image described above.

In Step S102, the postoperative information derivation unit 204 derives the bone mineral content $B_A$ at the position $X_A$ in the bone part of the subject relatively close to the artificial object. The position $X_A$ may be designated by the user.

In Step S103, the postoperative information derivation unit 204 derives the bone mineral content $B_B$ at the position $X_B$ in the bone part of the subject relatively far from the artificial object. The position $X_B$ may be designated by the user.

In Step S104, the postoperative information derivation unit 204 derives the numerical value K depending on the difference between the bone mineral content $B_A$ and the bone mineral content $B_B$, as the postoperative information. The postoperative information derivation unit 204 may derive, for example, $B_B$-$B_A$ or $B_A/B_B$ as the numerical value K.

In Step ST5, the postoperative information derivation unit 204 displays the postoperative information derived in Step ST4 on the display unit 104.

As described above, with information processing apparatus 10 according to the embodiment of the technique of the present disclosure, the postoperative information indicating the state of the bone part of the subject after the artificial object is implanted in the bone part of the subject is derived based on the bone mineral content around the artificial object implanted in the bone part of the subject. With this, it is possible to enable accurate recognition of the state of the bone part after the operation to implant the artificial object in the bone part of the patient as the subject is performed. Accordingly, it is possible to solve a problem that variation occurs in a diagnosis result in a case where a diagnosis method based on physician's visual confirmation of an image for diagnosis is applied.

In the embodiment, although a case where the numerical value K depending on the difference between the bone mineral content $B_A$ at the position $X_A$ relatively close to the artificial object and the bone mineral content $B_B$ at the position $X_B$ relatively far from the artificial object is derived as the postoperative information has been described, the technique of the present disclosure is not limited to the aspect. For example, the graph itself indicating a relationship between the distance from the artificial object and the bone mineral content shown in FIG. 7 may be derived as postoperative information.

The bone mineral content $B_A$ at the position $X_A$ relatively close to the artificial object and the bone mineral content $B_B$ at the position $X_B$ relatively far from the artificial object may be acquired for every predetermined period after the operation, and time transition of the numerical value K depending on the difference between the bone mineral contents $B_A$ and $B_B$ at each point of time may be derived as postoperative information.

Figure 11:
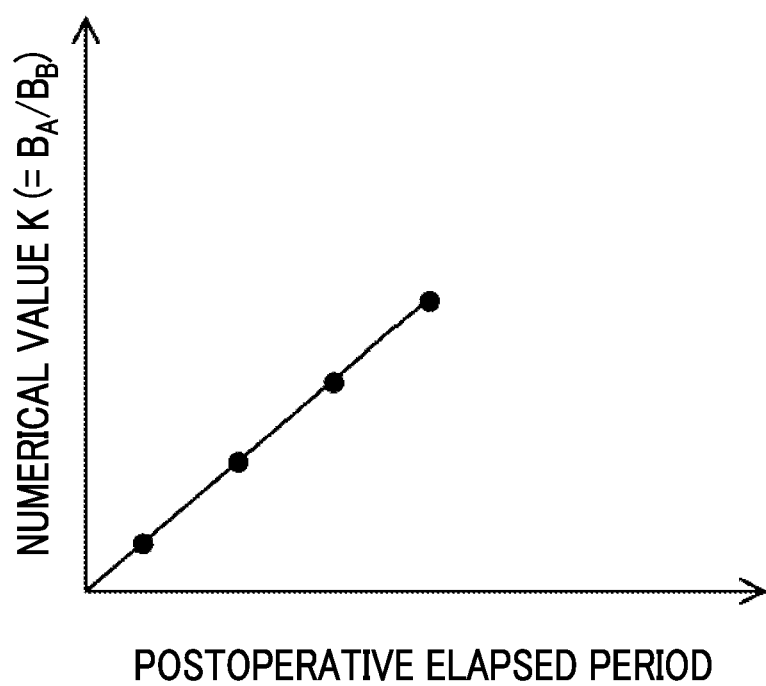
FIG. 11 is a graph showing an example of time transition of a numerical value K according to the embodiment of the technique of the present disclosure.

FIG. 11 is a graph showing an example of time transition of the numerical value K (=$B_A/B_B$). In a case of deriving the time transition of the numerical value K shown in FIG. 11 as the postoperative information, the information processing apparatus 10 acquires the first radiographic image G1 and the second radiographic image G2 for every predetermined period (for example, every week) after the operation, performs the generation of the bone part image Gb and the derivation of the bone mineral content B at each point of time, and stores the bone part image Gb and the bone mineral content B in the storage unit 103. The postoperative information derivation unit 204 derives the bone mineral content $B_A$ of each point of time at the position $X_A$ relatively close to the artificial object and the bone mineral content $B_B$ of each point of time at the position $X_B$ relatively far from the artificial object, derives the numerical value K (=$B_A/B_B$) at each point of time, and displays time transition of the derived numerical value K as postoperative information on the display unit 104. It is preferable that the position $X_A$ relatively close to the artificial object is coincident at each point of time, and it is preferable that the position $X_B$ relatively far from the artificial object is also coincident at each point of time. The positions $X_A$ and $X_B$ at each point of time can be registered, for example, with the artificial object as a reference.

The postoperative information derivation unit 204 may derive a slope of the graph shown in FIG. 11 as information indicating a speed of recovery of the bone part after the operation and may display the slope on the display unit 104. Alternatively, a determination result regarding the speed of recovery may be derived based on the slope of the graph and may be displayed on the display unit 104. For example, in a case where the slope of the graph is greater than a predetermined threshold value, a message indicating that recovery is going well may be displayed on the display unit 104, and in a case where the slope of the graph is smaller than the predetermined threshold value, a message indicating that recovery is slow may be displayed on the display unit 104. The postoperative information derivation unit 204 may display the numerical value K ($=B_A/B_B$) for every predetermined period after the operation in parallel on the display unit 104.

As described above, the time transition of the numerical value K is derived as the postoperative information, whereby it is possible to enable accurate recognition of a situation of recovery of the bone part after the operation. The postoperative information derivation unit 204 may derive time transition of a bone mineral content $B_A$ at a position $X_A$ relatively close to the stem 600 as postoperative information.

The postoperative information derivation unit 204 may derive a numerical value (for example, $B_C$-$B_A$ or $B_A/B_C$) depending on a difference between a bone mineral content $B_C$ around a planned implant region of the artificial object before the artificial object is implanted in the bone part of the subject and a bone mineral content $B_A$ around the artificial object after the artificial object is implanted in the bone part of the subject, as postoperative information. In this case, before the artificial object is implanted in the bone part of the subject, first and second radiographic images G1 and G2 are acquired for the patient as the subject, and a bone part image Gb is generated based on the first and second radiographic image G1 and G2. A bone mineral content B is derived for each pixel of the bone part image Gb. The preoperative bone mineral content B derived in this manner is stored in the storage unit 103. The postoperative information derivation unit 204 extracts the bone mineral content $B_C$ around the planned implant region of the artificial object among the preoperative bone mineral contents B stored in the storage unit 103 and derives the postoperative information based on the preoperative bone mineral content $B_C$ and the postoperative bone mineral content $B_A$ as described above.

In the embodiment, although a case where the first radiographic image G1 and the second radiographic image G2 are acquired from the first radiation detector 5 and the second radiation detector 6, respectively, has been described, the technique of the present disclosure is not limited to the aspect. For example, the first radiographic image G1 and the second radiographic image G2 may be acquired from a single radiographic detector. In this case, the first radiographic image G1 is acquired through irradiation of X-ray having a first energy distribution from the X-ray source 3, and the second radiographic image G2 is acquired through irradiation of X-ray having a second energy distribution different from the first energy distribution from the X-ray source 3.

In the embodiment, although the artificial bone has been described as an example of the artificial object, the technique of the present disclosure can also be applied to a case where a fastening member, such as a bolt, is implanted as an artificial object in the bone part.

Second Embodiment

Figure 12:
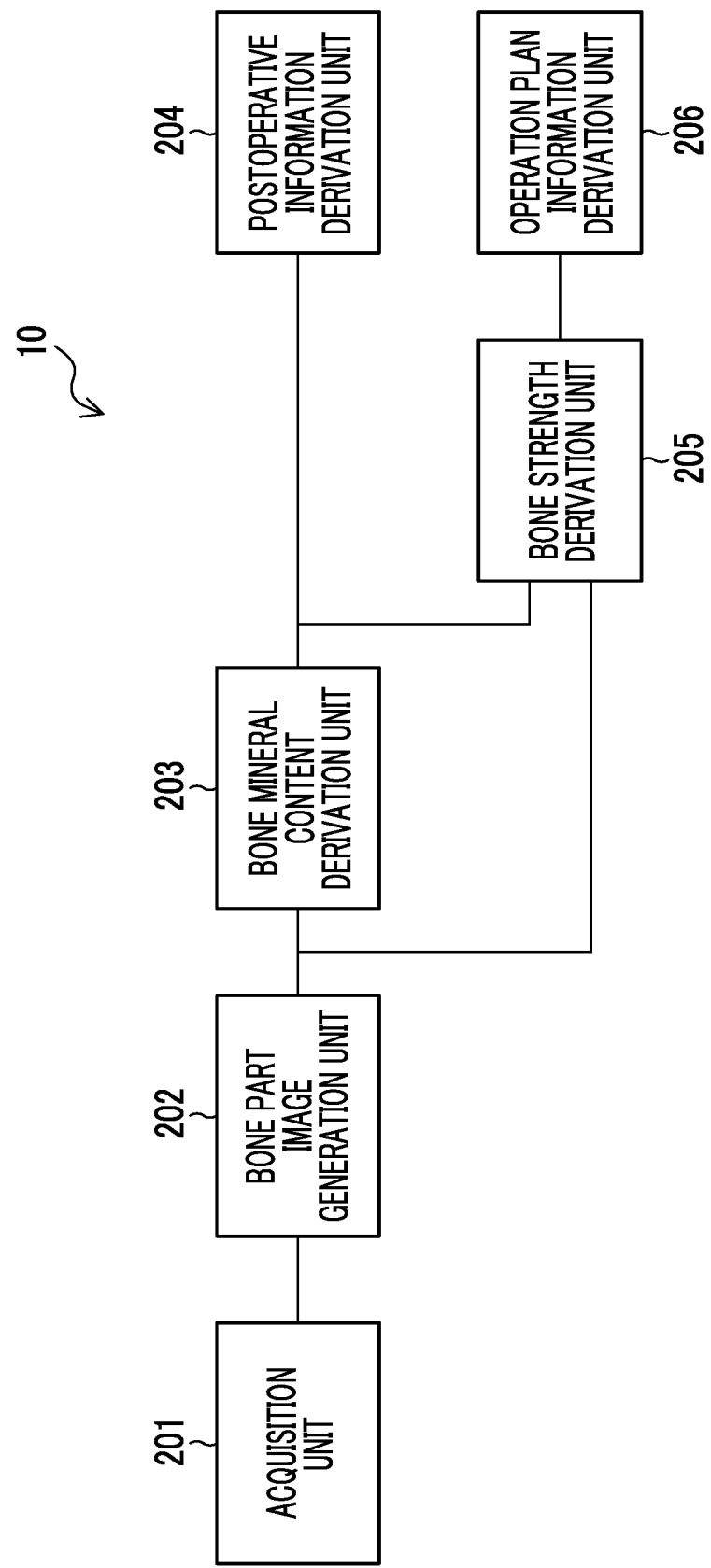
FIG. 12 is a functional block diagram showing an example of the functional configuration of an information processing apparatus according to another embodiment of the technique of the present disclosure.

FIG. 12 is a functional block diagram showing an example of the functional configuration of an information processing apparatus 10 according to a second embodiment of the technique of the present disclosure. The information processing apparatus 10 comprises a bone strength derivation unit 205 and an operation plan information derivation unit 206, in addition to the functional units (see FIG. 3) provided in the information processing apparatus 10 according to the first embodiment.

The bone strength derivation unit 205 derives bone strength S of each pixel of the bone part image Gb based on the bone mineral content B derived by the bone mineral content derivation unit 203 and an index value representing the texture of the bone. As the index value representing the texture, a numerical value obtained by quantifying a degree of density of bone trabecula structures forming the bone can be used. The degree of density of the bone trabecula structure can be quantified, for example, by a variance value $\sigma^2$ of a high frequency component of an image of the bone part region in the bone part image Gb. For example, as the density of the bone trabecula structure is lower, the variance value $\sigma^2$ is smaller. Accordingly, in the embodiment, the bone strength derivation unit 205 extracts the high frequency component of the image of the bone part region in the bone part image Gb, for example, using a method using Fourier transformation, wavelet transformation, or a high-pass filter and derives the variance value $\sigma^2$ of the high frequency component of each pixel of the bone part region as the index value representing the texture of the bone. The bone strength derivation unit 205 performs multiplication between corresponding pixels for the bone mineral content B and the variance value $\sigma^2$ derived for each pixel, thereby deriving the bone strength S for each pixel of the bone part image Gb. That is, the bone strength S is represented by Expression (3) described below.

$$S(x,y)=\sigma^2(x,y) \times B(x,y) \tag{3}$$

As the index value representing the texture of the bone, a texture feature quantity by a cooccurrence matrix or the like, for example, uniformity, contrast, correlation, or entropy may be used. Here, the cooccurrence matrix is a matrix indicating a distribution of signal values of pixels in an image, and represents a frequency of a signal value of a pixel adjacent to a pixel having a certain signal value, as a matrix.

The operation plan information derivation unit 206 derives operation plan information based on the bone strength S derived by the bone strength derivation unit 205. The operation plan information is information contributing to formulation of an operation plan that is performed in a case of performing an operation to implant an artificial object in a bone part of a patient. In the embodiment, the operation plan information derivation unit 206 derives a high strength part area Q that is an area of a region having bone strength higher than a predetermined threshold value $S_{TH}$ in a planned region where the artificial object is to be implanted. The operation plan information derivation unit 206 determines that the operation to implant the artificial object in the bone part of the patient is possible in a case where the derived high strength part area Q is equal to or greater than a predetermined threshold value $Q_{TH}$. On the other hand, the operation plan information derivation unit 206 determines that the operation to implant the artificial object in the bone part of the patient is impossible in a case where the derived high strength part area Q is less than the predetermined threshold value $Q_{TH}$. The operation plan information derivation unit 206 displays a determination result on the display unit 104.

Figure 13:
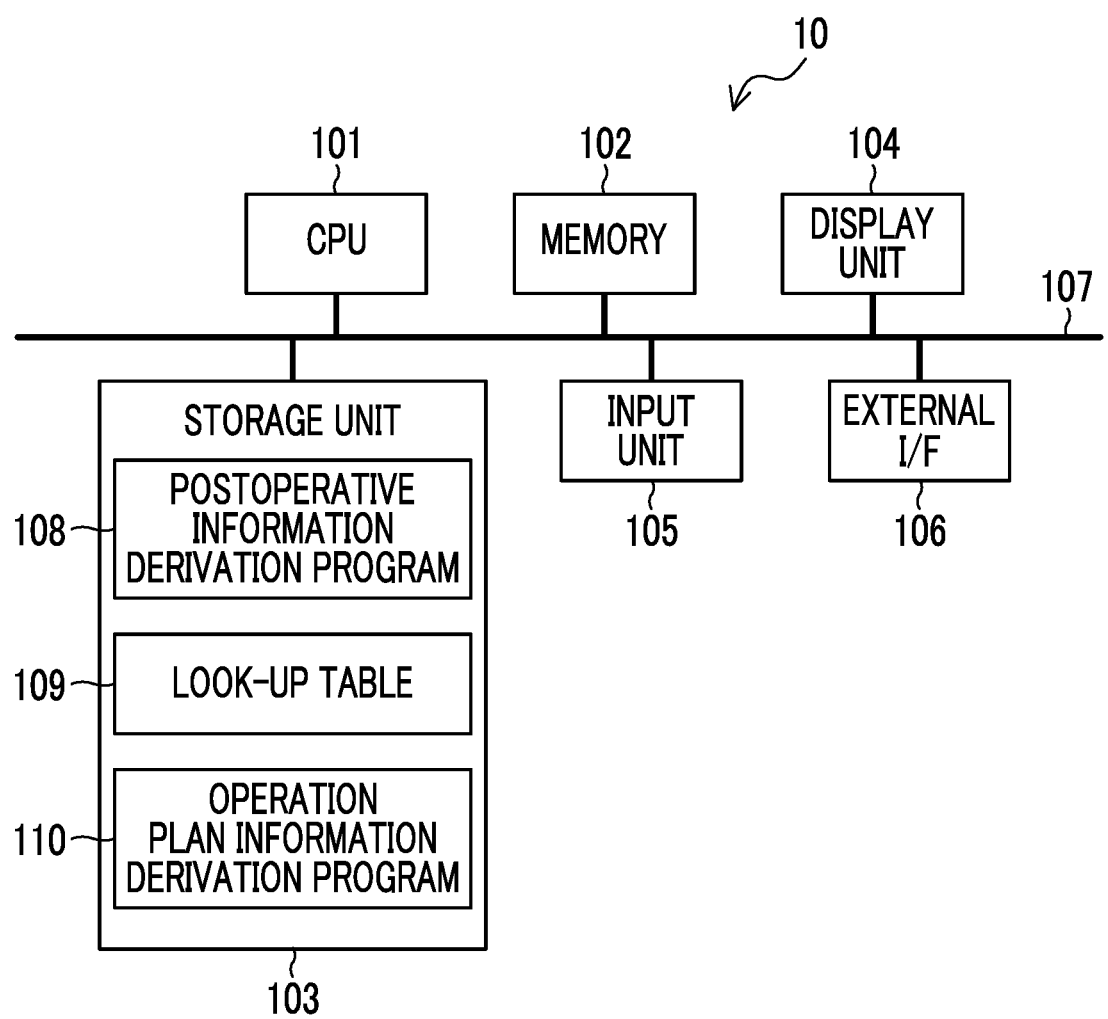
FIG. 13 is a diagram showing an example of the hardware configuration of the information processing apparatus according to another embodiment of the technique of the present disclosure.

FIG. 13 is a diagram showing an example of the hardware configuration of the information processing apparatus 10 according to the embodiment. The information processing apparatus 10 according to the embodiment is different from the information processing apparatus 10 according to the first embodiment in that an operation plan information derivation program 110 is stored in the storage unit 103. The information processing apparatus 10 functions as the acquisition unit 201, the bone part image generation unit 202, the bone mineral content derivation unit 203, the bone strength derivation unit 205, and the operation plan information derivation unit 206 by the CPU 101 executing the operation plan information derivation program 110.

Figure 14:
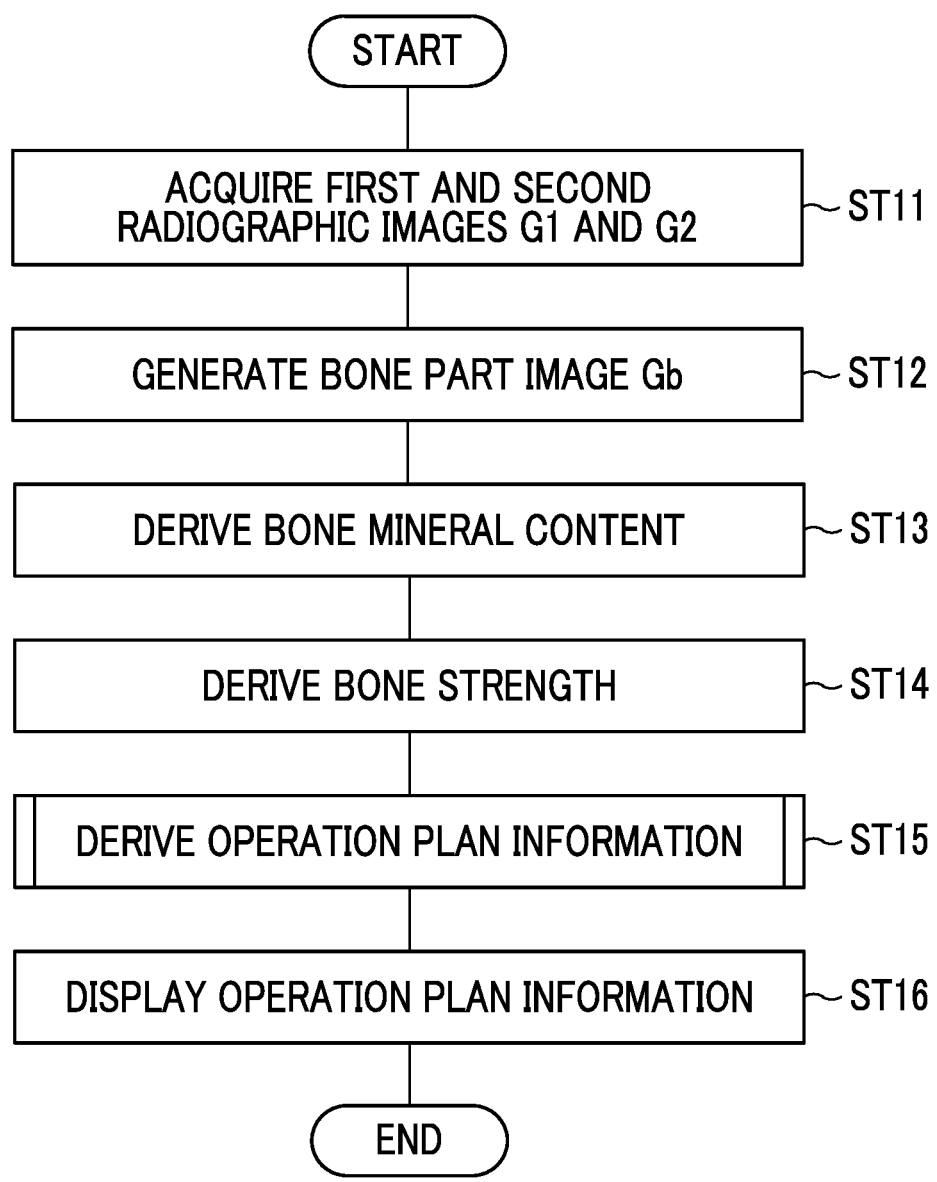
FIG. 14 is a flowchart illustrating an example of a flow of operation plan information derivation processing according to the embodiment of the technique of the present disclosure.

Hereinafter, the operations of the information processing apparatus 10 according to the second embodiment will be described. FIG. 14 is a flowchart illustrating an example of a flow of operation plan information derivation processing that is executed by the CPU 101 executing the operation plan information derivation program 110. The operation plan information derivation program 110 is executed, for example, in a case where an instruction to start execution is input by the user through the input unit 105.

In Step ST11, the acquisition unit 201 acquires the first radiographic image G1 and the second radiographic image G2 captured for the patient as the subject before the operation to implant the artificial object in the bone part is performed, from the first radiation detector 5 and the second radiation detector 6, respectively.

In Step ST12, the bone part image generation unit 202 performs weighting subtraction shown in Expression (1) between corresponding pixels in the first radiographic image G1 and the second radiographic image G2, thereby generating the bone part image Gb in which the bone part of the subject is highlighted.

In Step ST13, the bone mineral content derivation unit 203 derives the bone mineral content B for each pixel of the bone part image Gb by correcting each pixel value of the bone part image Gb using the correction coefficient acquired from the look-up table 109.

In Step ST14, the bone strength derivation unit 205 derives the bone strength for each pixel of the bone part image Gb based on the bone part image Gb derived in Step ST12 and the bone mineral content B derived in Step ST13. Specifically, the bone strength derivation unit 205 extracts the high frequency component of the image of the bone part region in the bone part image Gb generated in Step ST12, for example, using a method using Fourier transformation, wavelet transformation, or a high-pass filter. Next, the bone strength derivation unit 205 derives the variance value $\sigma^2$ of the high frequency component of each pixel of the bone part region as the index value representing the texture of the bone. Next, the bone strength derivation unit 205 performs multiplication $(B \times \sigma^2)$ between corresponding pixels for the derived variance value $\sigma^2$ and the bone mineral content B derived in Step ST13, thereby deriving the bone strength for each pixel of the bone part image Gb.

In Step ST15, the operation plan information derivation unit 206 derives the operation plan information based on the bone strength derived in Step ST14.

Figure 15:
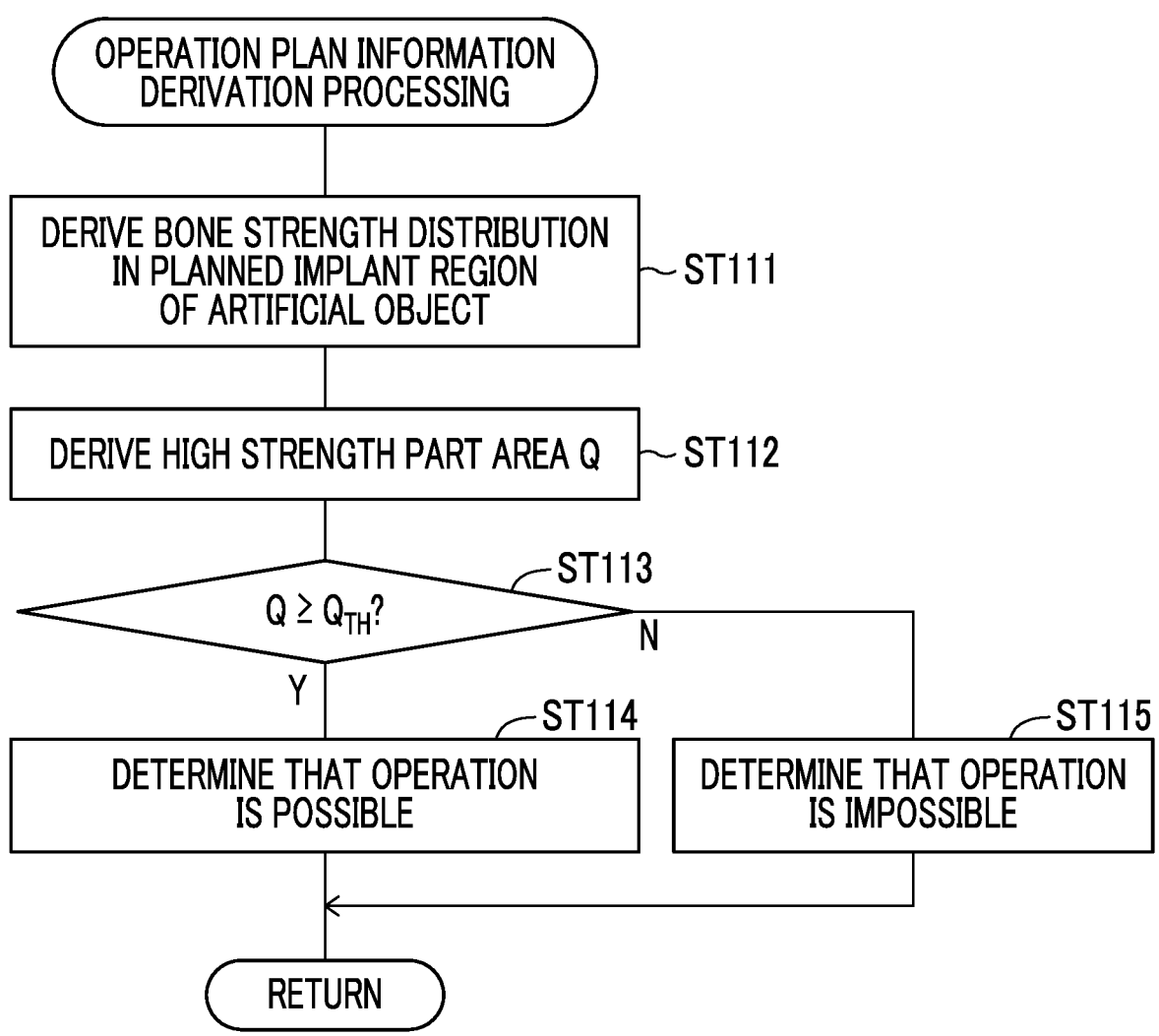
FIG. 15 is a flowchart illustrating an example of processing of deriving operation plan information according to the embodiment of the technique of the present disclosure.

FIG. 15 is a flowchart illustrating an example of the processing that is executed in Step ST15. In Step ST111, the operation plan information derivation unit 206 derives a bone strength distribution in the planned region where the artificial object is to be implanted. The planned region where the artificial object is to be implanted may be designated by the user through the input unit 105, for example.

In Step S112, the operation plan information derivation unit 206 specifies the region having bone strength higher than the predetermined threshold value $S_{TH}$ in the planned region where the artificial object is to be implanted and derives the high strength part area Q that is the area of the specified region.

In Step S113, the operation plan information derivation unit 206 determines whether or not the high strength part area Q derived in Step S112 is equal to or greater than the threshold value $Q_{TH}$. The operation plan information derivation unit 206 progresses the process to Step S114 in a case where determination is made that the high strength part area Q is equal to or greater than the threshold value $Q_{TH}$, and progresses the process to Step S115 in a case where determination is made that the high strength part area Q is less than the threshold value $Q_{TH}$. In Step S114, the operation plan information derivation unit 206 determines that the operation is possible. In Step S115, the operation plan information derivation unit 206 determines that the operation is impossible.

In Step ST16, the operation plan information derivation unit 206 displays a determination result derived in Step ST15 on the display unit 104.

As described above, the information processing apparatus 10 according to the embodiment determines whether or not the operation to implant the artificial object in the bone part of the patient is possible, based on the bone strength of the bone part of the patient before the operation and presents the determination result as the operation plan information. In a case where the artificial object is implanted in a region where the bone strength is excessively low, the region may be damaged by the artificial object. Accordingly, it is preferable that, in a region where the artificial object is to be implanted, a region that has a given level or more of area depending on the size of the artificial object to be implanted and in which the bone strength is sufficiently high is secured. In a case where a region suitable for implanting the artificial object is not secured, it is considered that it is appropriate to not perform the operation to implant the artificial object. In a case of performing the operation to implant the artificial object in the bone part, an operation plan including determination regarding whether or not the operation is performable is formulated. With the information processing apparatus 10 according to the embodiment, it is possible to provide information contributing to the formulation of the operation plan that is performed in a case of performing the operation to implant the artificial object in the bone part of the patient.

The operation plan information derivation unit 206 may derive a recommended region where the artificial object is to be implanted in a case where determination is made that the operation to implant the artificial object in the bone part of the patient is possible and may display the recommended region on the display unit 104. For example, the operation plan information derivation unit 206 may derive a region where the bone strength is relatively high, among regions having bone strength higher than the threshold value $S_{TH}$, as the recommended region. For example, in a case where a plurality of regions having bone strength higher than the threshold value $S_{TH}$ are present discontinuously, a region having the greatest area may be derived as the recommended region.

In the embodiment, although a case where the operation plan information derivation unit 206 derives the operation plan information based on the bone strength derived by the bone strength derivation unit 205 has been described, the technique of the present disclosure is not limited to the aspect. The operation plan information derivation unit 206 may derive operation plan information based on the bone mineral content derived by the bone mineral content derivation unit 203. Specifically, the operation plan information derivation unit 206 derives an area Q of a region having a bone mineral content greater than a predetermined threshold value $B_{TH}$ in the planned region where the artificial object is to be implanted. The operation plan information derivation unit 206 determines that the operation to implant the artificial object in the bone part of the patient is possible in a case where the derived area Q is equal to or greater than a threshold value $Q_{TH}$. On the other hand, the operation plan information derivation unit 206 determines that the operation to implant the artificial object in the bone part of the patient is impossible in a case where the derived area Q is less than the threshold value $Q_{TH}$.

In the first embodiment described above, although a case where the postoperative information derivation unit 204 derives the postoperative information based on the bone mineral content B derived by the bone mineral content derivation unit 203 has been described, the technique of the present disclosure is not limited to the aspect. The postoperative information derivation unit 204 may derive postoperative information based on the bone strength derived by the bone strength derivation unit 205. Specifically, the postoperative information derivation unit 204 may derive a numerical value K (for example, $S_B - S_A$ or $S_A/S_B$) depending on a difference between bone strength $S_A$ at the position $X_A$ relatively close to the artificial object and bone strength $S_B$ at the position $X_B$ relatively far from the artificial object, as postoperative information.

Figure 16:
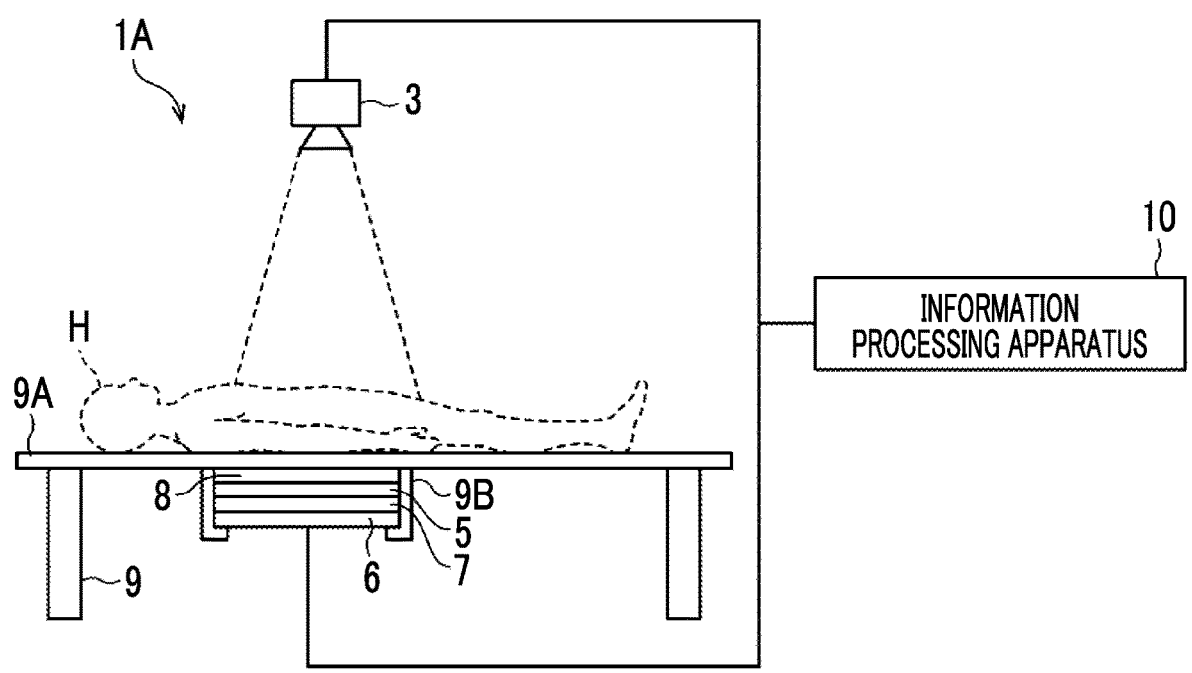
FIG. 16 is a schematic block diagram showing the configuration of another radiography system according to the embodiment of the technique of the present disclosure.

In the respective embodiments described above, although the subject H is imaged in an upright posture, as shown in FIG. 16, the subject H may be imaged in a decubitus posture. A radiography system 1A shown in FIG. 16 is a system that acquires a radiographic image of the subject H who is lying on an imaging table 9. In the radiography system 1A, in order from a side close to a X-ray source 3, a first radiation detector 5, a X-ray energy conversion filter 7, and a second radiation detector 6 are disposed. A scattered ray elimination grid (hereinafter, simply referred to as a grid) 8 that eliminates a scattered ray component scattered by the subject H in X-ray transmitted through the subject H is disposed between a tabletop 9A of the imaging table 9 and the first radiation detector 5. The grid 8, the first radiation detector 5, the X-ray energy conversion filter 7, and the second radiation detector 6 are attachably and detachably attached to the imaging table 9 by an attachment part 9B provided on a lower surface of the tabletop 9A of the imaging table 9.

In a case where the radiography system 1A shown in FIG. 16 is used, the tabletop 9A of the imaging table 9 and the grid 8 are interposed between the subject H and the first radiation detector 5. In the radiography system 1 shown in FIG. 1 and the radiography system 1A shown in FIG. 16, air may be interposed between the subject H and the first radiation detector 5 at the time of imaging. In such a case, X-ray transmitted through the subject H is transmitted through the tabletop 9A, the grid 8, and in addition, an air layer, and the first radiation detector 5 is irradiated with X-ray. Here, an object, such as the tabletop 9A, the grid 8, and the air, has unique radiation characteristics. For this reason, the quality of a primary ray component and a scattered ray component transmitted through the subject H changes depending on the radiation characteristics of the object by being transmitted through the object. Accordingly, in the embodiment, in performing the estimation of the body thickness distribution and the elimination of the scattered ray component using the first radiographic image G1, it is preferable to take into consideration the radiation characteristics of the object interposed between the subject H and the first radiation detector 5.

Specifically, primary ray transmittance and scattered ray transmittance of X-ray depending on the type of the object interposed between the subject H and the first radiation detector 5 are generated in a form of a table or the like in advance depending on various imaging conditions and the body thickness distribution of the subject H and are stored in the storage unit 103. Then, the bone mineral content derivation unit 203 acquires the radiation characteristics of the object depending on the body thickness distribution, that is, the primary ray transmittance and the scattered ray transmittance of X-ray with reference to the table in estimating the body thickness distribution of the subject H. The bone mineral content derivation unit 203 acquires an estimated primary ray image and an estimated scattered ray image using the acquired radiation characteristics, the imaging conditions, and the body thickness distribution, and composes the estimated primary ray image and the estimated scattered ray image to generate an estimated image. The generation of the estimated image and the correction of the body thickness distribution are repeatedly performed until a difference between the estimated image and the first radiographic image G1 satisfies a predetermined end condition. With this, the bone mineral content derivation unit 203 derives the body thickness distribution in a case where the end condition is satisfied, as the body thickness distribution $T(x,y)$ of the subject H. In the bone part image generation unit 202, the estimated scattered ray image in a case where the body thickness distribution satisfying the end condition is acquired is subtracted from the first radiographic image G1, whereby it is possible to eliminate the scattered ray component from the first radiographic image G1 taking into consideration the radiation characteristics of the object interposed between the subject H and the first radiation detector. The scattered ray component can also be eliminated from the second radiographic image G2 in a similar manner.

As the hardware structures of processing units that execute various kinds of processing, such as the functional units of the information processing apparatus 10 in the above-described embodiments, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like, in addition to a CPU that is a general-purpose processor executing software (program) to function as various processing units, as described above.

One processing unit may be configured of one of various processors described above or may be configured of a combination of two or more processors (for example, a combination of a plurality of FPGAs or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

In the above-described embodiments, although an aspect where the postoperative information derivation program 108 and the operation plan information derivation program 110 are stored (installed) in the storage unit 103 in advance has been described, the technique of the present disclosure is not limited thereto. The postoperative information derivation program 108 and the operation plan information derivation program 110 may be provided in a form of being recorded on a recording medium, such as a compact disc read only memory (CD-ROM), a digital versatile disc read only memory (DVD-ROM), or a universal serial bus (USB) memory. Alternatively, the postoperative information derivation program 108 and the operation plan information derivation program 110 may be in a form of being downloaded from an external apparatus through a network.

From the above description, it is possible to ascertain the technique related to the following supplementary item.

[Supplementary Item]

An information processing apparatus comprising:
a processor; and
a memory incorporated in or connected to the processor, in which the processor is configured to
generate a bone part image in which a bone part of a subject is highlighted, from a first radiographic image and a second radiographic image acquired by radiation having different energy distributions transmitted through the subject,
derive a bone mineral content for each pixel of the bone part image, and
based on a bone mineral content around an artificial object implanted in the bone part of the subject, derive information indicating a state of the bone part of the subject after the artificial object is implanted in the bone part of the subject, as postoperative information.

What is claimed is:

1. An information processing apparatus comprising at least one processor, wherein the processor is configured to generate a bone part image in which a bone part of a subject is highlighted, from a first radiographic image and a second radiographic image acquired by radiation having different energy distributions transmitted through the subject;
derive a body thickness distribution of the subject;
obtain a correction coefficient corresponding to the body thickness distribution of the subject and the imaging conditions when the first and second radiographic images were obtained by referring to a lookup table that specifies the body thickness of the subject and the correction coefficient for various imaging conditions;
derive a bone mineral content for each pixel of the bone part image by multiplying the correction coefficient by the pixel value of the bone image;
based on a bone mineral content around an artificial object implanted in the bone part of the subject, derive information indicating a state of the bone part of the subject after the artificial object is implanted in the bone part of the subject, as postoperative information;
display the postoperative information on a display; and
wherein the processor is configured to derive a difference value or ratio value between a bone mineral content at a first position relative to the artificial object and a bone mineral content at a second position relative to the artificial object, as the postoperative information, wherein the first position and the second position are along a line from the artificial object, and wherein the first position is closer to the artificial object than the second position.

2. The information processing apparatus according to claim 1,
wherein the processor is configured to derive information indicating time transition of the numerical value, as the postoperative information.

3. The information processing apparatus according to claim 1,
wherein the processor is configured to derive information indicating a relationship between a distance from the artificial object to a bone mineral content, as the postoperative information.

4. The information processing apparatus according to claim 1,
wherein the processor is configured to derive a numerical value depending on a difference between a bone mineral content around a planned implant region of the artificial object before the artificial object is implanted in the bone part of the subject and the bone mineral content around the artificial object after the artificial object is implanted in the bone part of the subject, as the postoperative information.

5. The information processing apparatus according to claim 1,
wherein the processor is configured to specify a region of a cancellous bone forming the bone part based on the bone mineral content of each pixel of the bone part image and derives information indicating a state of the cancellous bone of the subject based on a bone mineral content of the cancellous bone around an artificial object implanted in the cancellous bone of the subject, as the postoperative information.

6. The information processing apparatus according to claim 1,
wherein the processor is configured to specify regions of a cancellous bone and a cortical bone forming the bone part based on the bone mineral content of each pixel of the bone part image and derives information indicating the state of the bone part of the subject based on a bone mineral content of at least one of the cancellous bone or the cortical bone around the artificial object implanted in the bone part of the subject, as the postoperative information.

7. The information processing apparatus according to claim 1, wherein the processor is further configured to derive bone strength for each pixel of the bone part image based on the bone mineral content of each pixel of the bone part image.

8. The information processing apparatus according to claim 1, wherein the processor is further configured to derive an area of a region having a bone mineral content greater than a predetermined threshold value or bone strength higher than a predetermined threshold value in a planned region where the artificial object is implanted, based on the bone mineral content or bone strength of each pixel of the bone part image and determines whether or not an operation to implant the artificial object in the bone part of the subject is possible, based on the area.

9. The information processing apparatus according to claim 8,
wherein the processor is configured to derive a recommended region where the artificial object is to be implanted, based on the bone mineral content or bone strength of each pixel of the bone part image.

10. The information processing apparatus according to claim 1,
wherein the processor is configured to eliminate a scattered ray component from the first radiographic image and the second radiographic image based on a radiation characteristic of an object interposed between the subject and a radiation detector for acquiring the first radiographic image or the second radiographic image.

11. An information processing method comprising:
generating a bone part image in which a bone part of a subject is highlighted, from a first radiographic image and a second radiographic image acquired by radiation having different energy distributions transmitted through the subject;
deriving a body thickness distribution of the subject;
obtaining a correction coefficient corresponding to the body thickness distribution of the subject and the imaging conditions when the first and second radiographic images were obtained by referring to a lookup table that specifies the body thickness of the subject and the correction coefficient for various imaging conditions;
deriving a bone mineral content for each pixel of the bone part image by multiplying the correction coefficient by the pixel value of the bone image;
based on a bone mineral content around an artificial object implanted in the bone part of the subject, deriving information indicating a state of the bone part of the subject after the artificial object is implanted in the bone part of the subject, as postoperative information;
display the postoperative information on a display; and
deriving a difference value or ratio value between a bone mineral content at a first position relative to the artificial object and a bone mineral content at a second position relative to the artificial object, as the postoperative information, wherein the first position and the second position are along a line from the artificial object, and wherein the first position is closer to the artificial object than the second position.

12. A non-transitory computer-readable storage medium that stores a program causing a computer to execute a process comprising:
generating a bone part image in which a bone part of a subject is highlighted, from a first radiographic image and a second radiographic image acquired by radiation having different energy distributions transmitted through the subject;
deriving a body thickness distribution of the subject;
obtaining a correction coefficient corresponding to the body thickness distribution of the subject and the imaging conditions when the first and second radiographic images were obtained by referring to a lookup table that specifies the body thickness of the subject and the correction coefficient for various imaging conditions;
deriving a bone mineral content for each pixel of the bone part image by multiplying the correction coefficient by the pixel value of the bone image;
based on a bone mineral content around an artificial object implanted in the bone part of the subject, deriving information indicating a state of the bone part of the subject after the artificial object is implanted in the bone part of the subject, as postoperative information;
display the postoperative information on a display; and
deriving a difference value or ratio value between a bone mineral content at a first position relative to the artificial object and a bone mineral content at a second position relative to the artificial object, as the postoperative information, wherein the first position and the second position are along a line from the artificial object, and wherein the first position is closer to the artificial object than the second position.

* * * * *